(12) United States Patent
Steele et al.

(10) Patent No.: US 7,092,826 B2
(45) Date of Patent: *Aug. 15, 2006

(54) SEMICONDUCTOR WAFER INSPECTION SYSTEM

(75) Inventors: M. Brandon Steele, Decatur, GA (US); Jeffrey Alan Hawthorne, Decatur, GA (US)

(73) Assignee: Qcept Technologies, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/156,088

(22) Filed: Jun. 17, 2005

(65) Prior Publication Data

US 2005/0234658 A1  Oct. 20, 2005

Related U.S. Application Data

(63) Continuation of application No. 10/631,469, filed on Jul. 29, 2003, now Pat. No. 6,957,154.

(60) Provisional application No. 60/444,504, filed on Feb. 3, 2003.

(51) Int. Cl.
  *G01B 5/28* (2006.01)
  *H01L 21/00* (2006.01)
  *B08B 6/00* (2006.01)

(52) U.S. Cl. .............. 702/35; 702/36; 438/12; 134/1.3

(58) Field of Classification Search ............ 702/35, 702/36, 34, 81; 324/765; 438/12, 200, 906; 134/1.2, 1.3
See application file for complete search history.

(56) References Cited

U.S. PATENT DOCUMENTS

| 4,166,974 | A | 9/1979 | Vermeers |
| 4,295,092 | A | 10/1981 | Okamura |
| 4,481,616 | A | 11/1984 | Matey |
| 4,973,910 | A | 11/1990 | Wilson |
| 5,087,533 | A | 2/1992 | Brown |
| 5,136,247 | A | 8/1992 | Hansen |
| 5,214,389 | A | 5/1993 | Cao et al. |
| 5,217,907 | A | 6/1993 | Bulucea et al. |
| 5,218,362 | A | 6/1993 | Mayes et al. |
| 5,270,664 | A | 12/1993 | McMurtry et al. |

(Continued)

FOREIGN PATENT DOCUMENTS

DE        297509 A5    1/1992

(Continued)

OTHER PUBLICATIONS

B Scruton and B.H. Blott, A High Resolution Probe for Scanning Electrostatic Potential Profiles Across Surfaces; Journal of Physics E: Scientific Instruments (May 1973), pp. 472-474; vol. 6, No. 5, Printed in Great Britain.

(Continued)

*Primary Examiner*—Michael Nghiem
*Assistant Examiner*—Meagan S Walling
(74) *Attorney, Agent, or Firm*—Foley & Lardner LLP

(57) ABSTRACT

A method and system for identifying a defect or contamination on a surface of a material. The method and system involves providing a material, such as a semiconductor wafer, using a non-vibrating contact potential difference sensor to scan the wafer, generate contact potential difference data and processing that data to identify a pattern characteristic of the defect or contamination.

28 Claims, 12 Drawing Sheets

U.S. PATENT DOCUMENTS

| | | | |
|---|---|---|---|
| 5,272,443 | A | 12/1993 | Winchip et al. |
| 5,278,407 | A | 1/1994 | Ikebe et al. |
| 5,293,131 | A | 3/1994 | Semones et al. |
| 5,315,259 | A | 5/1994 | Jostlein |
| 5,369,370 | A | 11/1994 | Stratmann et al. |
| 5,381,101 | A | 1/1995 | Bloom et al. |
| 5,460,684 | A | 10/1995 | Saeki et al. |
| 5,517,123 | A | 5/1996 | Zhao et al. |
| 5,546,477 | A | 8/1996 | Knowles et al. |
| 5,583,443 | A | 12/1996 | McMurtry et al. |
| 5,723,980 | A | 3/1998 | Haase et al. |
| 5,723,981 | A | 3/1998 | Hellemans et al. |
| 5,773,989 | A | 6/1998 | Edelman et al. |
| 5,974,869 | A | 11/1999 | Danyluk et al. |
| 5,977,788 | A | 11/1999 | Lagowski |
| 6,011,404 | A | 1/2000 | Ma et al. |
| 6,037,797 | A | 3/2000 | Lagowski et al. |
| 6,091,248 | A | 7/2000 | Hellemans et al. |
| 6,094,971 | A | 8/2000 | Edwards et al. |
| 6,097,196 | A | 8/2000 | Verkuil et al. |
| 6,114,865 | A | 9/2000 | Lagowski et al. |
| 6,127,289 | A | 10/2000 | Debusk |
| 6,139,759 | A | 10/2000 | Doezema et al. |
| 6,198,300 | B1 | 3/2001 | Doezema et al. |
| 6,201,401 | B1 | 3/2001 | Hellemans et al. |
| 6,232,134 | B1 | 5/2001 | Farber et al. |
| 6,255,128 | B1 | 7/2001 | Chacon et al. |
| 6,265,890 | B1 | 7/2001 | Chacon et al. |
| 6,517,669 | B1 | 2/2003 | Chapman |
| 6,520,839 | B1 | 2/2003 | Gonzalez-Martin et al. |
| 6,538,462 | B1 | 3/2003 | Lagowski et al. |
| 6,546,814 | B1 | 4/2003 | Cloe et al. |
| 6,551,972 | B1 | 4/2003 | Lei et al. |
| 6,597,193 | B1 | 7/2003 | Lagowski et al. |
| 6,664,546 | B1 | 12/2003 | McCord et al. |
| 6,664,800 | B1 | 12/2003 | Chacon et al. |
| 6,679,117 | B1 | 1/2004 | Danyluk et al. |
| 6,680,621 | B1 | 1/2004 | Savtchouk et al. |
| 6,711,952 | B1 | 3/2004 | Leamy et al. |
| 6,717,413 | B1 | 4/2004 | Danyluk et al. |
| 2002/0140564 | A1 | 10/2002 | Danyluk et al. |
| 2002/0186036 | A1 | 12/2002 | Smith |
| 2003/0052374 | A1 | 3/2003 | Lee et al. |
| 2003/0129776 | A1 | 7/2003 | Eom et al. |
| 2003/0139838 | A1 | 7/2003 | Marcella |
| 2003/0164942 | A1 | 9/2003 | Take |
| 2003/0175945 | A1 | 9/2003 | Thompson et al. |
| 2004/0029131 | A1 | 2/2004 | Thompson et al. |
| 2004/0057497 | A1 | 3/2004 | Lagowski et al. |
| 2004/0058620 | A1 | 3/2004 | Gotkis et al. |
| 2004/0105093 | A1 | 6/2004 | Hamamatsu et al. |
| 2004/0134515 | A1 | 7/2004 | Castrucci |
| 2004/0152250 | A1* | 8/2004 | Steele et al. ............... 438/200 |

FOREIGN PATENT DOCUMENTS

| | | |
|---|---|---|
| EP | 1039277 | 3/2000 |
| EP | 1304463 | 4/2003 |
| WO | WO 01/90730 A2 | 11/2001 |
| WO | WO 2004/070355 A2 | 8/2004 |

OTHER PUBLICATIONS

Yano D et al: "Nonvibrating contact potential difference probe measurement of a nanometer-scale lubricant on a hard disk", Journal of Tribology, American Society of Mechanical Engineers, New York, NY, US; vol. 121, No. 4, Oct. 1999, pp. 980-983, XP008031092, ISSN: 0742-4787 (pp. 980-981, fig. 4, first ref. on p. 983).

Castaldini A et al: "Surface analyses of polycrystalline and Cz-Si wafers", Solar Energy Materials and Solar Cells, Elsevier Science Publishers, Amsterdam, NL; vol. 72, No. 1-4, Apr. 2002, pp. 425-432, XP004339790, ISSN: 0927-0248 (whole document).

Korach C S et al: "Measurement of perfluoropolyether lubricant thickness on a magnetic disk surface", Applied Physics Letters, American Institute of Physics, New York, NY, US: vol. 79, No. 5, Jul. 30, 2001, pp. 698-700, XP012029958, ISSN: 0003-6951 (p. 699, left column; fig. 2).

Yang Y et al: "Kelvin probe study on the perfluoropolyether film on metals", Tribology Letters, 2001, Kluwer Academic/Plenum Publishers, USA, vol. 10, No. 4, pp. 211-216, XP009035197, ISSN: 1023-8883 (p. 211-p. 212).

Castaldini A et al: "Scanning Kelvin probe and surface photovoltage analysis of multicrystalline silicon", Materials Science and Engineering B., Elsevier Sequoia, Lausanne, CH; vol. 91-92, Apr. 30, 2002, pp. 234-238, XP004355534, ISSN: 0921-5107 (chapters 2.2 Scanning Kelvin probe: and "4.2 Scanning Kelvin probe analyses").

Lagel B et al: "A novel detection system for defects and chemical contamination in semiconductors based upon the scanning Kelvin probe", 14th International Vacuum Congress (IVC-14). 10th International Conference on Solid Surfaces (ICS-10). 5th International Conference on Nanometre-Scale Science and Technology (NANO-5). 10th International Conference on Quantitative Surface Analysis; vol. 433-435, pp. 622-626, XP002292441, Surface Science, Aug. 2, 1999, Elsevier, NL, ISSN: 003906028 (whole document).

Ren J et al: "Scanning Kelvin Microscope: a new method for surface investigations" 8. Arbeitstagtung Angewandte Oberflachenanalytik 'AOFA 8' ('Applied Surface Analysis'), Kaiserslautern, DE, Sep. 5-8, 1994; vol. 353, No. 3-4, pp. 303-306, XP009035181, Fresenius' Jounal of Analytical Chemistry, Oct. 1995, Springer-Verlag, DE, ISSN: 0937-0633 (p. 304, right column; fig. 1).

Baumgartner H et al: "Micro Kelvin probe for local work-function measurements", Review of Scientific Instrumetns, May 1988, USA; vol. 59, No. 5, pp. 802-805, XP0022922442, ISSN: 0034-6748 (abstract; fig. 4, chapter "V. Results").

Danyluk S: "Non-vibrating contact potential imaging for semiconductor fabrication", Semicon West 2003, 'Online!, Jul. 14, 2003, pp. 1-15, XP002292443, 'retrieved from the internet: ,URL:http://dom.semi.org/web/wFiles.nsf/Lookup/TIS18_QceptTechnologiesInc/$file/TIS18%20QceptTechnologiesInc.Alternate.pdf. retrieved on Aug. 13, 2004 (whole document).

Moorman, M. et al., "A Novel, Micro-Contact Potential Difference Probe," Sensors and Actuators B, Elsevier Sequoia S.A., Lausanne, CH, vol. 94, No. 1.

Reid, Jr., Lennox Errol, "Surface Characterization of Hard Disks Using Non-Contact Work Function Capacitance Probe," A Thesis Presented to the Academic Faculty in Partial Fulfillment of the Requirements for the Degree of Master of Science in Mechanical Engineering, Georgia Institute of Technology, Jun. 1986.

* cited by examiner

SEMICONDUCTOR WAFER INSPECTION SYSTEM

CROSS-REFERENCE OF PRIOR APPLICATION

This application is a continuation of U.S. application Ser. No. 10/631,469,filed Jul. 29, 2003, which claims priority to U.S. Application Ser. No. 60/444,504, filed on Feb. 3, 2003 both of which are incorporated herein by reference.

FILED OF THE INVENTION

The present invention is directed to a method and system for inspection of semiconductor wafers and other materials. More particularly, the invention is directed to a method and system for characterization of microscopic and macroscopic defects through imaging and visualization of contact potential difference topology on a wafer or material surface through use of a non-vibrating contact potential difference (hereinafter NVCPD) sensor.

BACKGROUND OF THE INVENTION

The multi-billion dollar global market for semiconductor defect management is growing both in absolute terms and as a percentage of semiconductor capital equipment investment. In general, there are two factors that determine the economics of a semiconductor fabrication facility at a given utilization level, namely throughput and yield. As complex new technologies such as 300 mm wafers, copper interconnects, and reduced feature (circuit) sizes drive the margin of error in fabrication ever lower, new inspection technologies are critical to keep yields high and bottom-line economics attractive. Detection and elimination of chemical contamination and other types of defects is a constant concern for semiconductor manufacturers and equipment suppliers. Contamination can arise from use of processing chemicals, processing equipment and poor handling techniques. Contaminants can include for example metals, carbon and organic compounds. Other types of defects can result from a wide range of causes, including flaws in the semiconductor crystal, improper processing, improper handling, and defective materials. In addition, many cleaning steps are required in semiconductor wafer fabrication. Each step is time consuming and requires expensive chemicals that may require special disposal procedures. Existing methods for monitoring or controlling these processes are expensive and time consuming. As a result, wafers are often cleaned for a longer period of time and using more chemicals than are required.

Defect detection and characterization systems can be divided into in-line and off-line systems. "In-line" refers to inspection and measurement that takes place inside the clean room where wafers are processed. "Off-line" refers to analysis that takes place outside of the wafer processing clean room, often in a laboratory or separate clean room that is located some distance from the manufacturing area. In addition, many of these analytical techniques are destructive, which requires either the sacrifice of a production wafer or the use of expensive "monitor" wafers for analysis. In-line inspection and measurement is crucial for rapidly identifying and correcting problems that may occur periodically in the manufacturing process. A typical wafer can undergo over 500 individual process steps and require weeks to complete. Each wafer can have a finished product value of up to $100,000. Because the number of steps, and period of time, involved in wafer fabrication are so large, a lot of work in process can exist at any point in time. It is critical that process-related defects be found and corrected immediately before a large number (and dollar value) of wafers are affected.

Many types of defects and contamination are not detectable using existing in-line tools, and these are typically detected and analyzed using "off line" techniques (described below) such as Total Reflectance X-ray Fluorescence (TXRF), Vapor Phase Decomposition Inductively Coupled Plasma-Mass Spectrometry (VPD ICP-MS) or Secondary Ion Mass Spectrometry (SIMS). Since these techniques are used off-line (outside of the clean room used to process wafers) and usually occur hours, or even days, after the process step that has caused the contamination, their value is significantly limited.

A brief description of some well known techniques for wafer inspection and chemical contamination detection are presented in Table 1. This list is not in any sense exhaustive as there are a very large number of techniques that are used for some type of semiconductor analysis or characterization.

TABLE 1

| Analytical Technique | Description | In-line/ Off-line |
|---|---|---|
| Total Reflection X-Ray Fluorescence (TXRF) | X-rays irradiate the wafer within the critical angle for total external reflectance, causing surface atoms to fluoresce. | Off-line |
| Automated Optical Microscopy | Optical images are acquired and automatically analyzed for detection of large defects. | In-line |
| Laser Backscattering | Wafer surface is illuminated with laser spots and the angle and/or polarization of reflected light is analyzed to detect and classify particles. | In-line |
| Vapor Phase Decomposition Inductively Coupled-Mass Spectrometry (VPD ICP-MS) | Wafers "scanned" with a drop of HF that is analyzed using mass spectrometry. | Off-line |
| Secondary Ion Mass Spectroscopy (SIMS) | Ion beam sputters the wafer surface creating secondary ions that are analyzed in a mass spectrometer. | Off-line |

Table 2 summarizes some major advantages and disadvantages of each technique. In general, off-line detection techniques are extremely sensitive to tiny amounts of contamination; but are slow, expensive and complex to operate. Some have limited, or no, imaging or surface mapping capability, or are destructive in nature. In-line techniques are much faster, non-destructive and provide defect mapping, but have limited chemical contamination detection or analysis capability.

TABLE 2

| Analytical Technique | Advantages | Disadvantages |
|---|---|---|
| Total Reflection X-Ray Fluorescence (TXRF) | Very sensitive Some mapping capability Nondestructive | Slow (>1 hour/wafer) Limited coverage Unpatterned wafers only |

TABLE 2-continued

| Analytical Technique | Advantages | Disadvantages |
|---|---|---|
| Automated Optical Microscopy | Fast<br>Relatively low cost<br>Detects a wide range of macro defects (>50 microns)<br>Imaging of wafer surface<br>Non-contact/non-destructive | Very limited chemical and particle detection |
| Laser Backscattering | Fast<br>Relatively low cost<br>Detects very small particles<br>Imaging of water surface<br>Non-contact/non-destructive | Only detects particles - no chemistry |
| Vapor Phase Decomposition Inductively Coupled-Mass Spectrometry (VPD ICP-MS) | Very sensitive<br>Able to identify wide range of contaminants<br>Only works on bare silicon | Destructive<br>Slow<br>Expensive<br>Complex<br>Cannot image |
| Secondary Ion Mass Spectroscopy (SIMS) | Very sensitive<br>Detects a wide range of contaminants<br>Detects sub-surface | Expensive<br>Slow<br>Destructive |

In general, existing in-line wafer inspection tools operate at production speeds and generate images of the wafer surface that are processed to identify and locate defects. These techniques, however, are as mentioned above very limited in their ability to detect chemical contamination. Laser backscattering systems are limited to detecting particles down to sub-micron sizes, and optical microscopy systems can only detect chemical contamination that results in a visible stain or residue. Both techniques lack the ability to identify or classify the chemical composition of the particle or contamination. Off-line laboratory techniques are used to qualify the cleanliness of new processes and equipment, or to analyze defects detected by in-line equipment or as part of failure analysis. A critical need therefore exists for a fast, inexpensive and effective means of detecting, locating and classifying relatively small quantities of chemical contamination on production wafers.

It is therefore an object of the invention to provide an improved method and system for inspection of surfaces of materials, such as semiconductor wafers.

It is an additional object of the invention to provide an improved method and system for providing images of surface defects on an semiconductor wafer.

It is yet another object of the invention to provide an improved method and system for identifying different classes of semiconductor wafer surface defects by pattern recognition.

It is still a further object of the invention to provide an improved method and system for classifying categories of surface defects on semiconductor wafers, including without limitation surface defect states, electrostatic field variations, oxide states and chemical contamination.

It is also an additional object of the invention to provide an improved method and system for sensing electrostatic fields arising from semiconductor wafer surface defects.

It is yet another object of the invention to provide an improved method and system for detecting the presence of thin dielectric films on surfaces of semiconductor wafers and to detect film defects such as pinholes, bubbles, delaminations, or contamination under the film.

It is a further object of the invention to provide an improved method and system to sense variations in oxide states on semiconductor wafer surfaces.

It is also a further object of the invention to provide an improved method and system to classify particulate contaminants on semiconductor wafers identified initially by optical inspection systems.

It is yet a further object of the invention to provide an improved method and system for detecting variations in dopant concentration of semiconductor wafers.

It is another object of the invention to provide an improved method and system for use of an NVCPD sensor to inspect the surface quality of semiconductor wafers.

It is still another object of the invention to provide an improved method and system of NVCPD sensors in combination with other inspection systems for evaluating semiconductor wafer surface properties.

It is a further object of the invention to provide an improved method and system for producing topological images of differing contact potential characteristic of defects on a semiconductor wafer.

It is also an object of the invention to provide an improved method and system for rapidly scanning the surface of a semiconductor wafer to identify sub-microscopic, microscopic and macroscopic surface defects characterized by potential field disturbances on the wafer surface.

It is also an object of the invention to provide an improved method and system for detecting the cleanliness of a semiconductor wafer to determine if a cleaning process has eliminated all contaminants and to avoid the time and expense of cleaning wafers for longer than is necessary to remove contaminants.

In each case described above, wafer surface can refer to the front-side (patterned side) of the wafer, back-side (unpatterned side) of the wafer, or the edge of the wafer.

Other objects, features and advantages of the present invention will be readily apparent from the following description of the preferred embodiment thereof, taken in conjunction with the accompanying drawings described below.

DETAILED DESCRIPTION OF PREFERRED EMBODIMENTS

Figure 1:
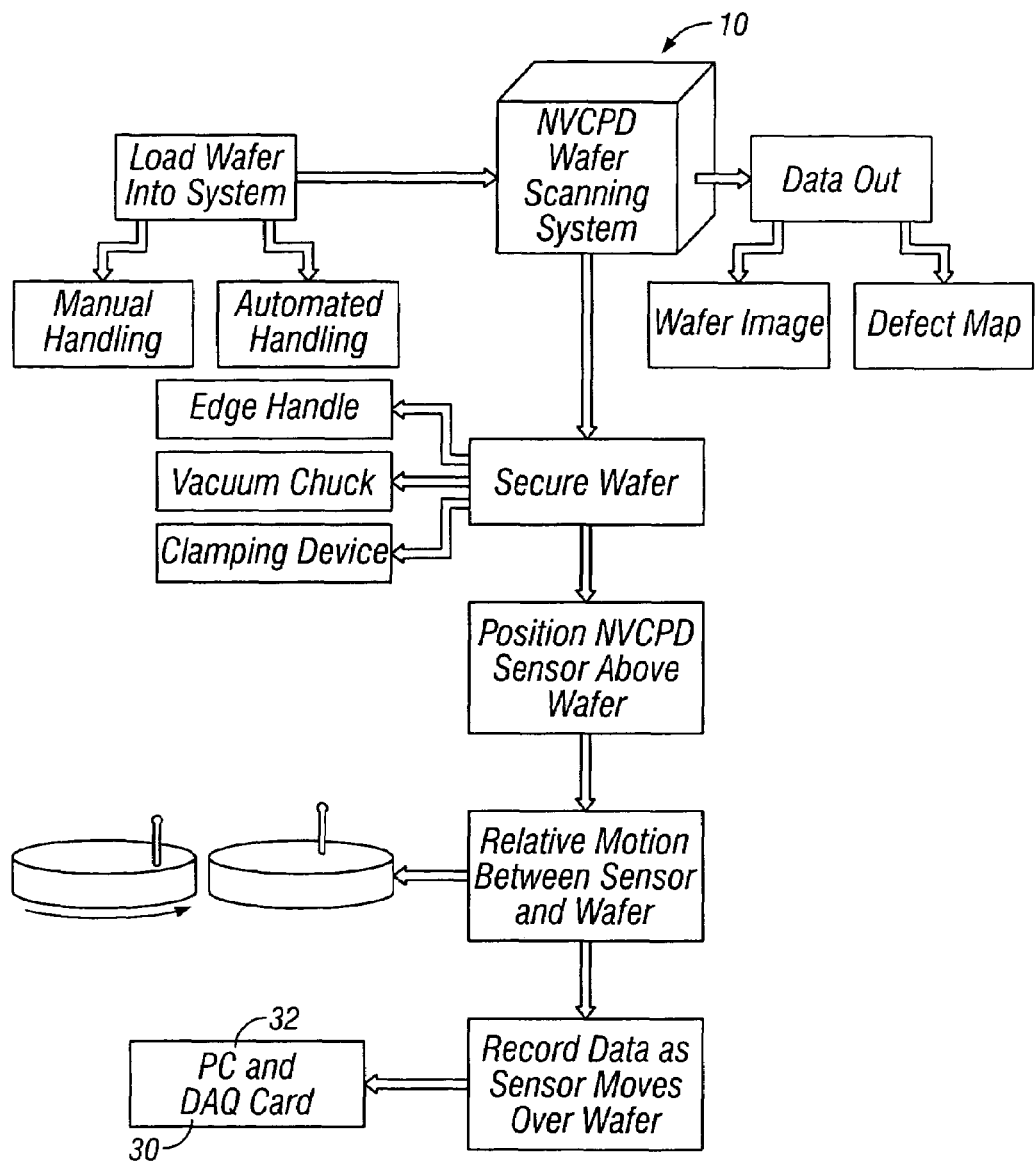
FIG. 1 illustrates one embodiment of the NVCPD scanning method and system.
Figure 2:
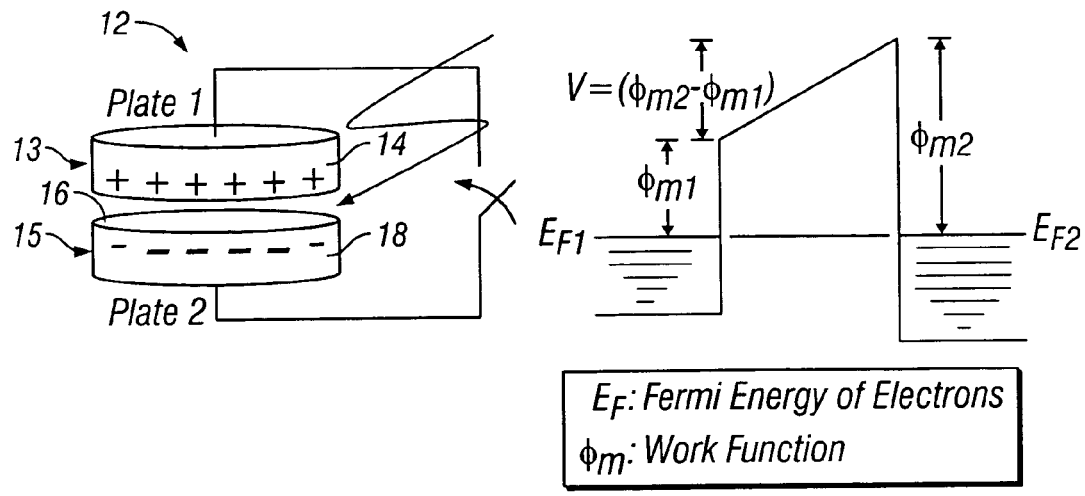
FIG. 2 illustrates the concept of the contact potential difference methodology.
Figure 3:
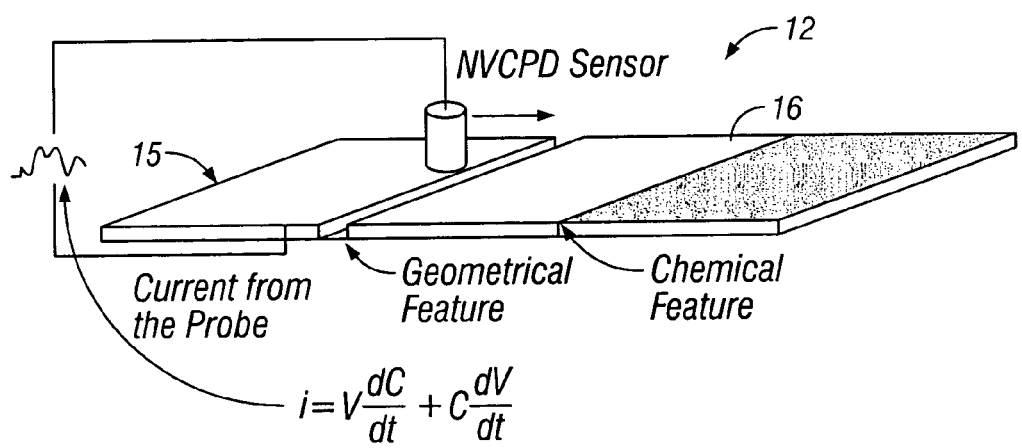
FIG. 3 illustrates an NVCPD scanning method.

The preferred embodiment of the invention is directed to an improved use of an NVCPD sensor. In particular, FIG. 1 illustrates a functional block flow diagram of components and operation of one preferred form of an NVCPD scanning system 10. NVCPD sensor 12 (see FIG. 2) is based on the phenomena of contact potential difference which is a voltage generated between two dissimilar materials brought in close proximity to each other. An illustration of this concept can be seen in FIG. 2. In the case of the wafer scanning system 10, the sensor tip 13 forms plate 14 and wafer 15 having a wafer surface 16 forms plate 18 (see FIG. 2.) Probe tip surface 20 of the plate 14 is made of a conducting material with a fixed work function. The wafer surface 16 of the plate 18 has a work function which can vary due to irregularities in the semiconductor wafer surface 16 or contaminants or other materials deposited on the wafer surface 16. When the two plates 14 and 18 are electrically connected, the Fermi levels of the respective surface equilibrate and form an electric field between them. If the work function of the sensor tip 13 is fixed, the magnitude of the electric field is then related to the distance between the two plates 14 and 18, the relative dielectric between the plates 14 and 18 and the work function of the wafer surface 16. In practice the plates 14 and 18 equilibrate rapidly providing little to measure. To provide a current flow that can be measured, some relative motion of the sensor tip 12 to the wafer surface 16 must be realized. The NVCPD sensor 12 is moved over the surface at a substantially fixed distance and variations in the wafer surface 16 cause a current to flow. An illustration of this concept can be seen in FIG. 3. The current flow from this NVCPD sensor 12 can be modeled by the following equation.

C and V are defined as $$i = C\frac{\partial V}{\partial t} + V\frac{\partial C}{\partial t}$$

$$C = \frac{\varepsilon_o \varepsilon_r A}{d} \text{ and } V = \frac{\Phi_{probe} - \Phi_{wafer}}{|e|}$$

where $\epsilon_0$ is the permittivity of free space, $\epsilon_r$, is the relative dielectric constant, A is the area of the probe tip, d is the distance between the sensor tip 13 and the wafer 15, $\Phi$ is the work function of the respective surface, and e is the charge on an electron. The V term can also be described as a difference in surface potentials between the NVCPD sensor 12 and the wafer 15. In addition the surface potentials on the wafer surface 16 can vary due to defects. The overall surface potential is related to the underlying materials work function but it can also be affected by adsorbed layers of material on the wafer surface 16. Even sub mono-layers of materials are known to significantly affect the surface potential.

Figure 4:
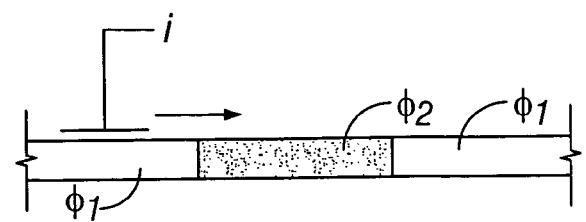
FIG. 4 illustrates the current output of an NVCPD probe as it passes over a positive and negative work function transition.
Figure 4:
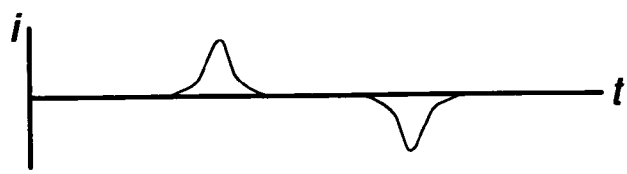

The $$C\frac{\partial V}{\partial t} \approx C\frac{\Phi_1 - \Phi_2}{\Delta t}$$

term is related to changes in work function on the wafer surface 16. It can be seen that the magnitude of this term is related to the relative changes in work function on the wafer surface 16 and relative speed at which the NVCPD sensor 12 is moved over the wafer surface 16. An illustration of the signal generated from this can be seen in FIG. 4.

Many defects can present themselves as variations in the wafer work function or the overall surface potential. For instance variation in semiconductor dopant concentrations in the wafer 15 will cause varying characteristic work functions. In addition other materials that could diffuse into the wafer 15 such as copper will cause variations in work function. Within the semiconductor material itself, mechanical phenomena such as dislocation pile-ups, cracks, and scratches generate local stresses which will change the local work function. In addition, adsorbed layers of atomic or molecular contaminants even at the sub monolayer level will generate appreciable surface potential variations. Particles deposited on the wafer 16 with a surface potential different than the surrounding wafer material will also create a signal. Layers of chemicals commonly used in the wafer fabrication process will affect the surface potential of the wafer. For instance residual CMP slurry or photo-resist would cause local variations in surface potential detectable by the NVCPD sensor 12.

The $$V\frac{\partial C}{\partial t}$$

term is related to changes in gap between the NVCPD sensor 12 and the wafer 15 or variations in the relative dielectric constant. Geometrical imperfections in the wafer surface 16 or particles on the wafer surface 16 would manifest themselves in this component. Also because of its differential nature the magnitude of this component would also increase as the relative speed of the NVCPD sensor 12 is increased.

Many classes of wafer defects would appear as geometrical changes in the wafer surface 16. In the wafer 15 itself surface cracks, scratches, etched trenches, etc. would be examples of this. In addition particles deposited on the wafer 15 would also present themselves as a local change in the distance to the probe sensor tip 13.

Variations of dielectric films on the wafer 15 can also be detected. An example would be detecting variations in the oxide state grown on the silicon substrate (i.e. $SiO$, $SiO_2$, $SiO_3$, $SiO_4$). In addition variations in dielectric of other non-conducting materials commonly deposited on the wafer could be detected.

It should also be noted that many features could present themselves as combinations of geometrical changes and chemical changes. For instance a particle deposited on the wafer 15 of differing material than the underlying wafer 15. Also a crack in the surface would also induce stresses that would cause variations in local work function.

Figure 5:
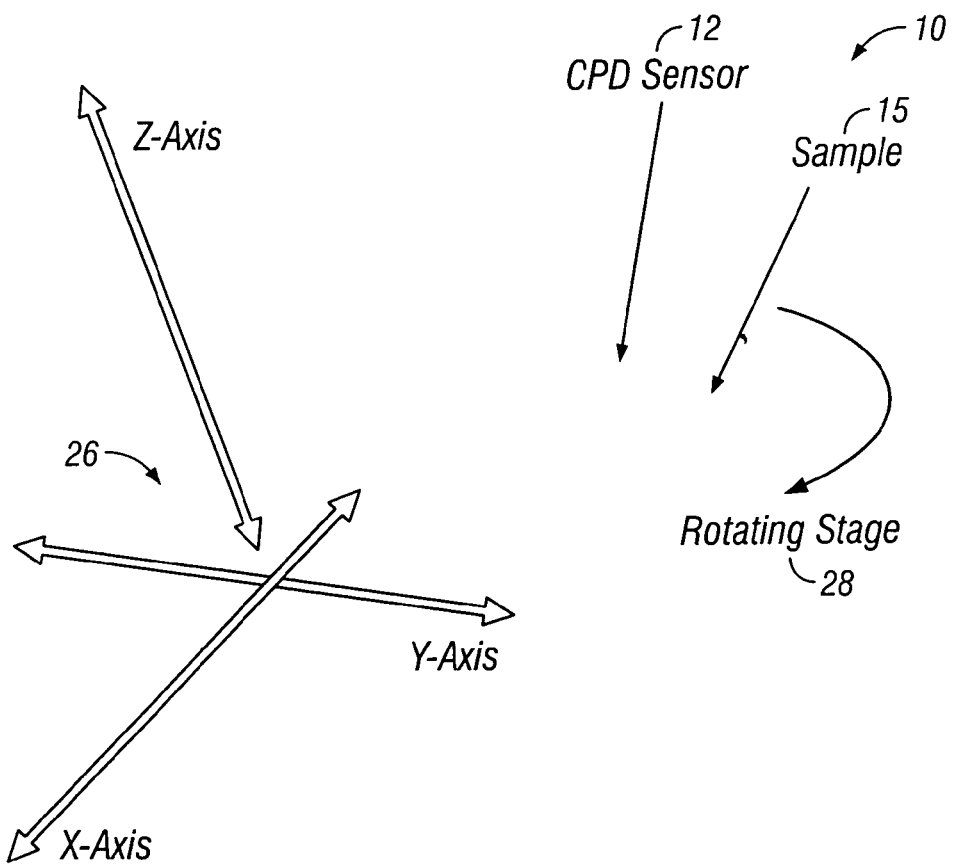
FIG. 5 illustrates axial orientation of the NVCPD system.
Figure 8A:
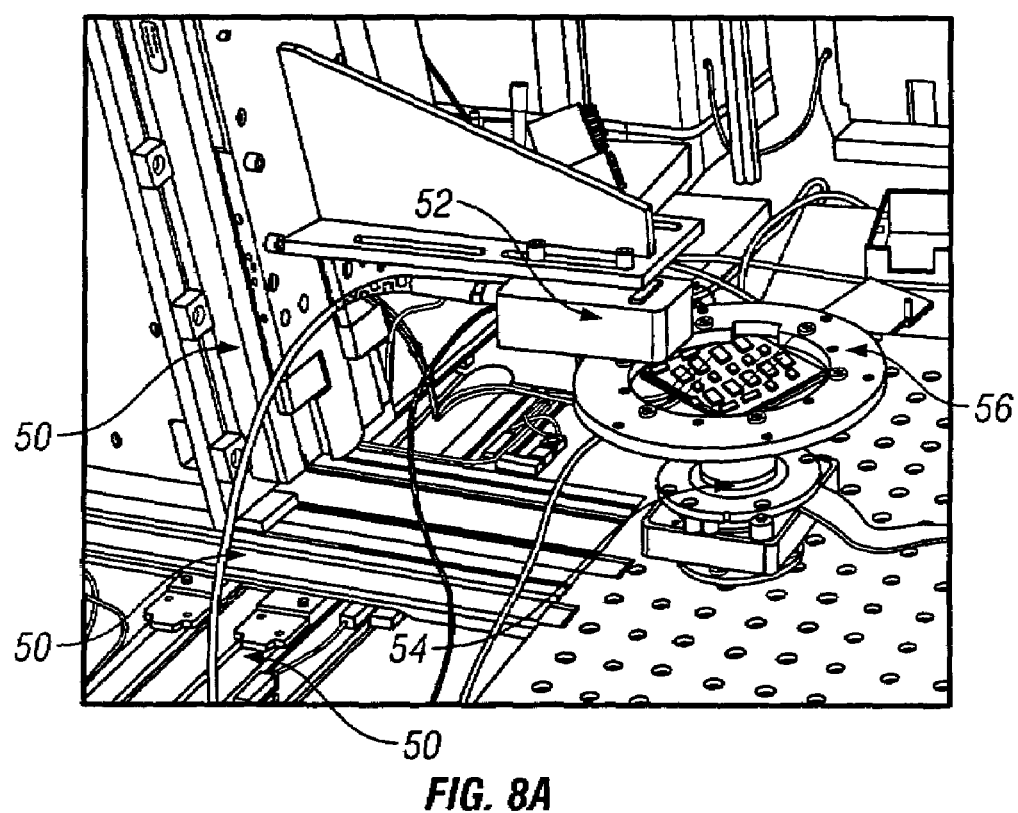
FIG. 8A illustrates one form of scanning NVCPD system with a three axis linear positioning system with the NVCPD sensor and a wafer mounted on a high speed spindle.
Figure 8B:
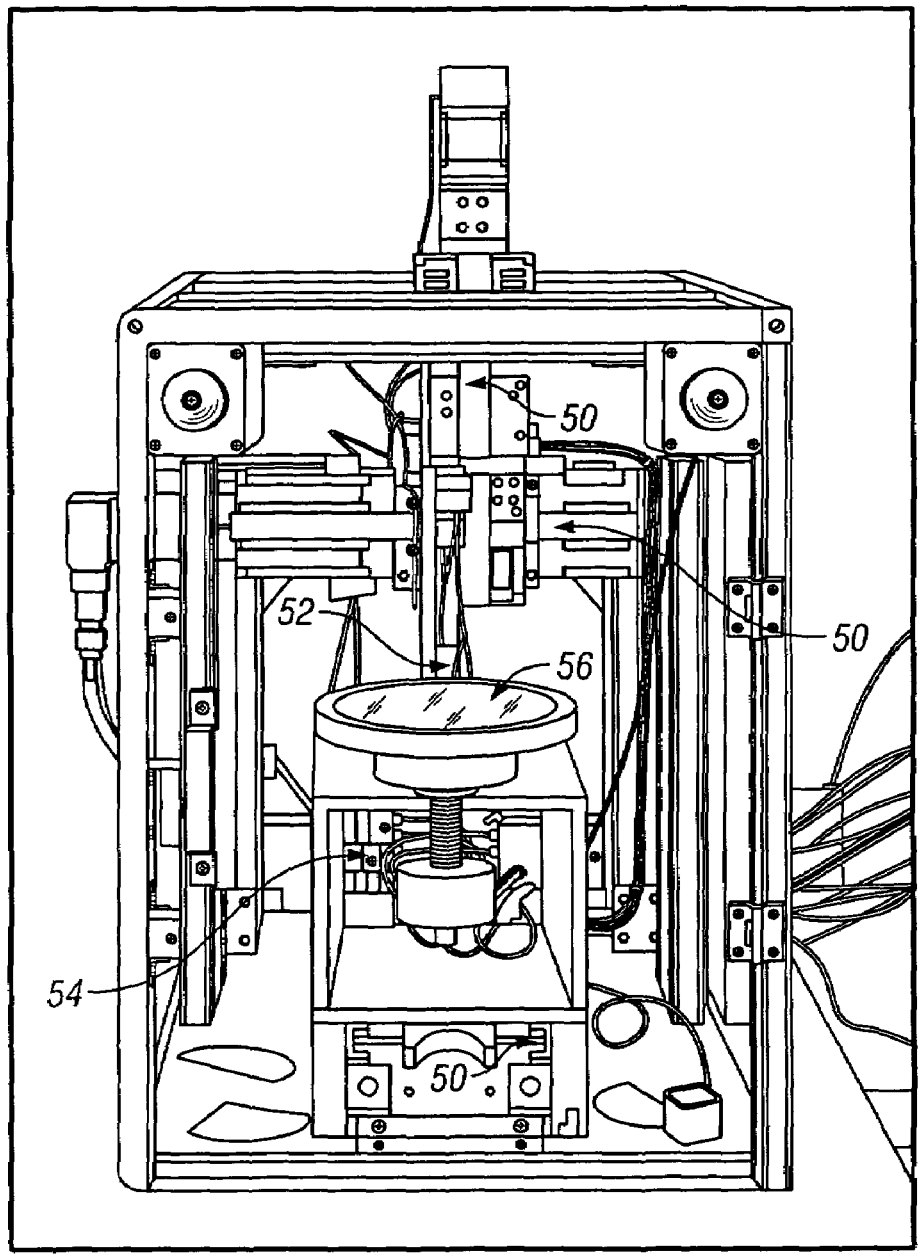
FIG. 8B illustrates another form of scanning NVCPD system.

In FIG. 5 is schematically shown one form of the system 10 for application of the NVCPD sensor 12 to scan the wafer 15 for defects and contamination. FIGS. 8A and 8B also illustrate more detailed drawings of two alternative operating embodiments of the system 10. The system 10 in FIG. 5 includes an X-Y-Z positioning system 26, a rotating wafer stage 28, a high speed data acquisition system 30 with a personal computer PC 32 and control software executed by the PC 32.

As shown in more detail in FIG. 8A, the wafer 15 is affixed to a rotating spindle 54 (see FIG. 1) using clamping fixture 56 on the wafer edges. A sensor positioning system 50 includes an NVCPD sensor 52 positioned a fixed distance from the wafer 15 is mounted to the spindle 54. The wafer 15 (not seen in this view) is then rotated at high speed, and the NVCPD sensor 52 is translated radially to collect data in circumferential tracks. The scanning procedure as shown schematically in FIG. 9 lasts between a few seconds and several minutes, depending on the number of scanned tracks, the speed of the spindle 54, and the speed of the sensor positioning system 52. The tracks of data are then put together to form a CPD image. These CPD images allow the visualization of chemical and geometrical defects and thereby enable classification of the type of defect present on the wafer surface. Some examples of these CPD images can be seen in FIG. 10A–15 and are taken from a 100 mm wafer compared with optical images of the same wafer (see Example hereinafter).

Figure 6:
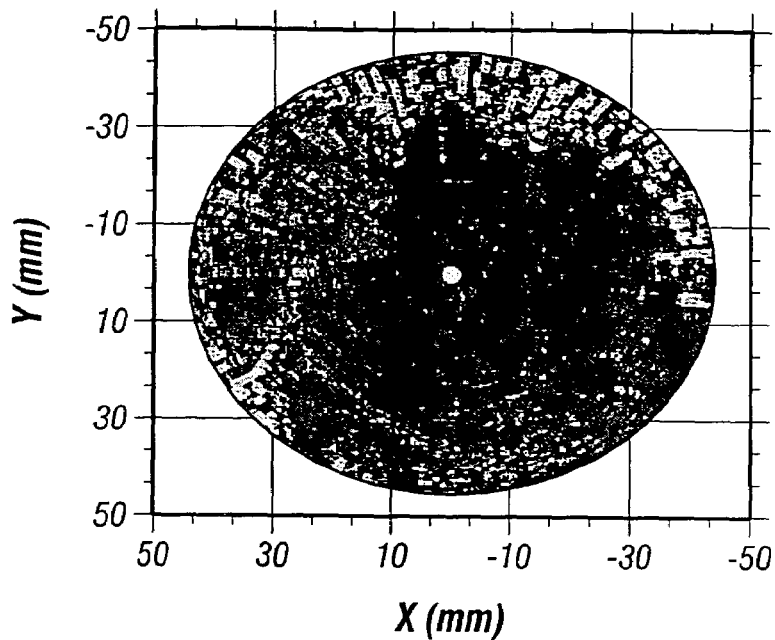
FIG. 6 illustrates standard deviation of signals within a scan area.

The images generated were subsequently processed to automatically locate defects. The idea behind this process was to locate areas of high variability. An ideal surface would exhibit a flat signal but a wafer surface with defects would exhibit some variability in the signal. To locate areas with defects the data was broken up in to small areas of known location. The standard deviation of the signal within these areas was determined. Areas with defects showed a higher standard deviation, and these results can be seen in FIG. 6. Areas with defects appear brighter than lower variability areas of the wafer 15. This is one of many possible methods to process the NVCPD data.

More generally, a defect can be identified by one or more of the following:

1. Process the data to look for a voltage or change in voltage (or pattern of voltages or changes in voltages) that exceeds some user-defined value (threshold).

2. Compare the data to a known pattern that represents a defect via some form of correlation or template matching.

3. Convert the spatial data to the frequency domain and then identify peaks in the frequency domain that represent defects with unique spatial characteristics.

These techniques can also be combined with other techniques to yield analytical results. The signal may also be preprocessed to facilitate defect detection, such as, for example:

1. Since the signal is differential, it can be integrated over some distance to produce voltages that represent relative CPD's over the surface of the wafer 15.

2. If the wafer 15 is "patterned", then this known pattern can be removed from the data prior to processing. This would likely be accomplished through some variation of image or signal subtraction in either the space or frequency domains.

3. The signal would likely be processed with some form of frequency filtering to remove high or low frequencies depending on the size, shape and other characteristics of the expected defects.

4. The signal could be processed to remove features of a certain size by doing what is called "morphological processing."

The following non-limiting example describes methods of preparation of test wafers and sensing characteristic images for identifying certain defect states, chemical states, electrostatic states and mechanical features present on a semiconductor wafer surface.

EXAMPLE

Sample wafers can be created by dip coating the wafer 15 in solutions that contain known concentrations of contaminants. Part of this example describes metal contaminants such as Cu and Fe, although any manner of chemical contaminants can be applied in this way. The wafer 15 described is either a 100 mm or 150 mm wafer, although these examples apply to any size wafer. The wafer surface 16 is prepared by dipping in HF to remove oxides. The wafer 15 is then cleaned and partially dipped in the metal contaminant solution. The amount of solution remaining on the wafer 15, and the resulting concentration of contaminant on the wafer surface 16, is controlled by selecting dip coating parameters such as the extraction rate.

Partial dipping of the test wafer 15 is preferred to create a transition from clean to contaminated areas. Because the NVCPD signal is differential, the NVCPD sensor 12 detects changes on the wafer surface 16, as opposed to an absolute value relating to surface condition. This aspect of NVCPD sensors 12 is offset by the ability to rapidly image and detect localized contamination anywhere on the surface of the wafer 15.

Figure 7:
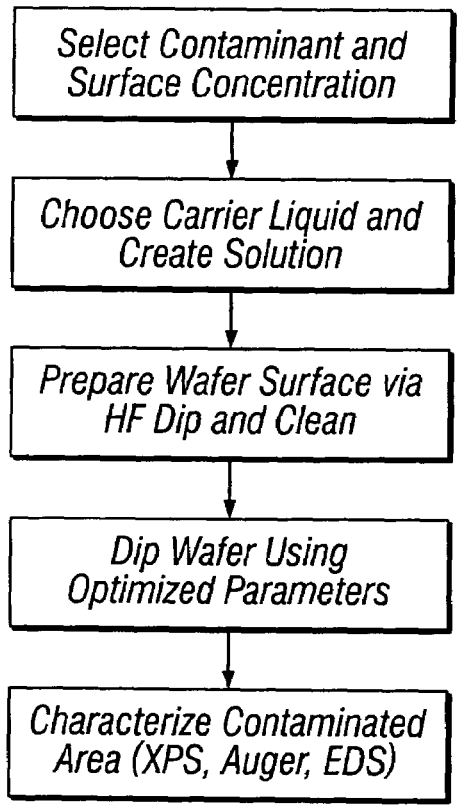
FIG. 7 illustrates steps for creating test wafers which are partially coated with known concentrations of contaminants.

After preparation, each test wafer 15 can be, if necessary, analyzed using an appropriate combination of XPS, Auger and RBS (or other well known surface analysis methods) techniques to determine actual contaminant concentrations in the dipped areas of the wafer 15. Each step involved in the sample wafer preparation process is shown in FIG. 7.

Figure 9:
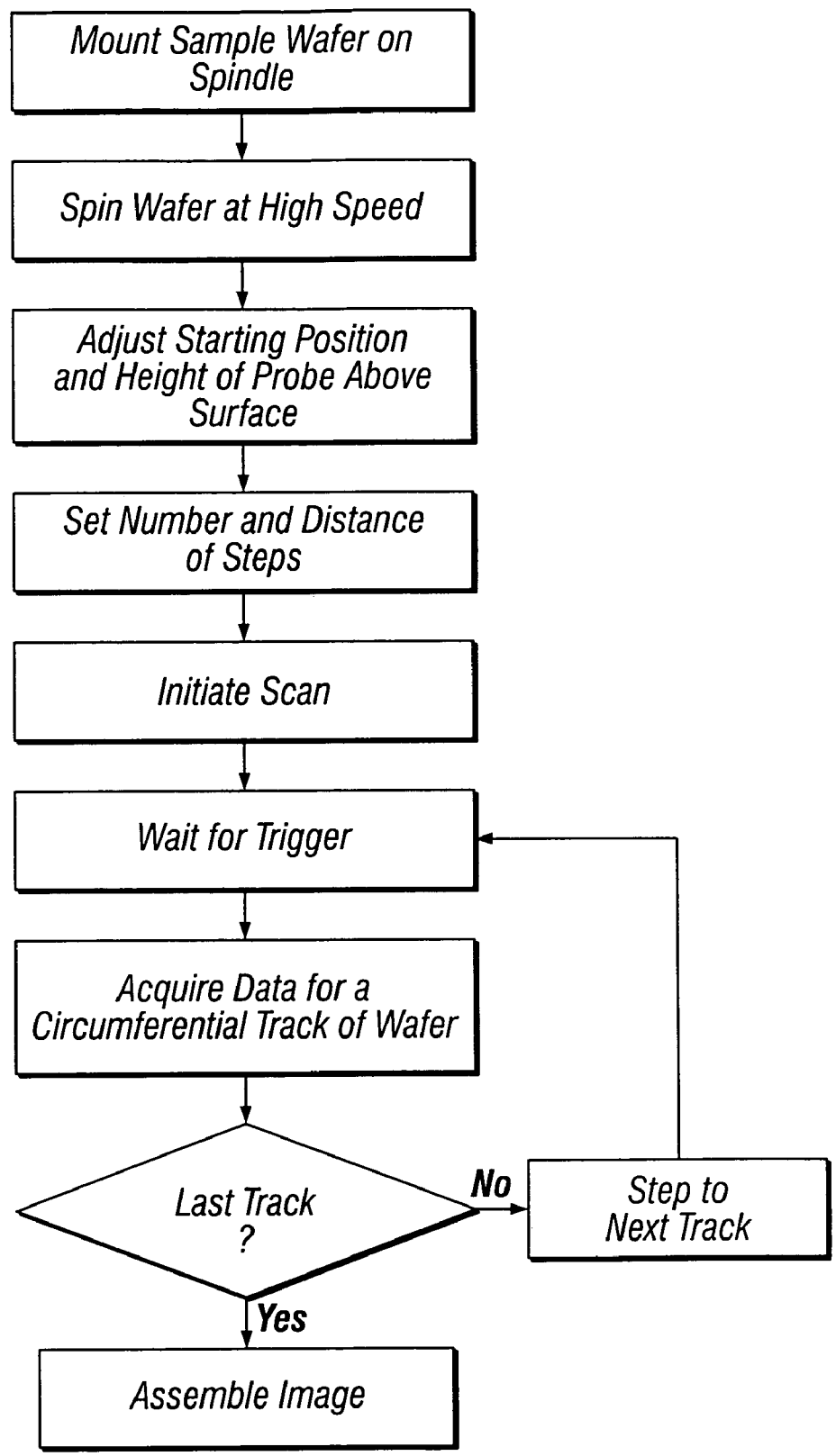
FIG. 9 illustrates a flow diagram for the image acquisition process of a radially scanned NVCPD imaging system.

After each sample wafer 15 is created, it can be imaged using a radially scanning NVCPD imaging system 10 constructed in accordance with the invention. As described before, FIGS. 8A and 8B show basic forms of the NVCPD imaging system 10, and FIG. 9 shows another flow diagram illustration of wafer processing. The system 10 employs the NVCPD sensor 12 mounted on the previously described three-axis positioning system 26. This positioning system 26 is used to position the NVCPD sensor 12 above the wafer surface 16 to be imaged, and to scan the NVCPD sensor 12 radially across the wafer surface. The wafer 15 is mounted on a spindle that rotates at high speed (1800 rpm) beneath the NVCPD sensor 12. The system 10 operates by acquiring multiple consecutive tracks of data as the NVCPD sensor 12 is stepped along the radius of rotation of the wafer 15.

Figure 10A:
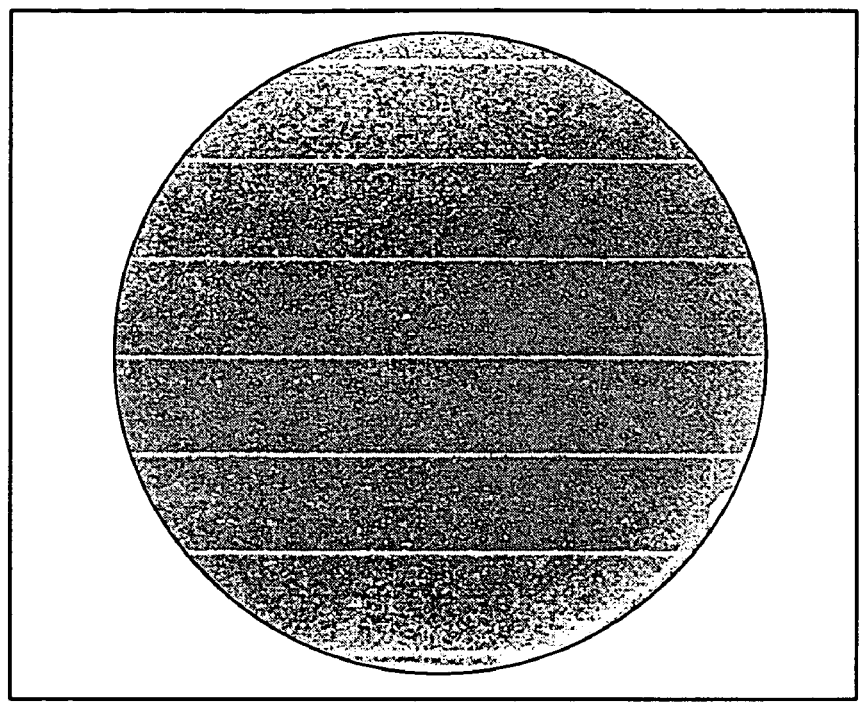
FIG. 10A illustrates an optical image of a 100 mm diameter silicon wafer after application of a vacuum pick-up device and FIG. 10B illustrates an NVCPD image of the wafer of FIG. 10A.
Figure 10B:
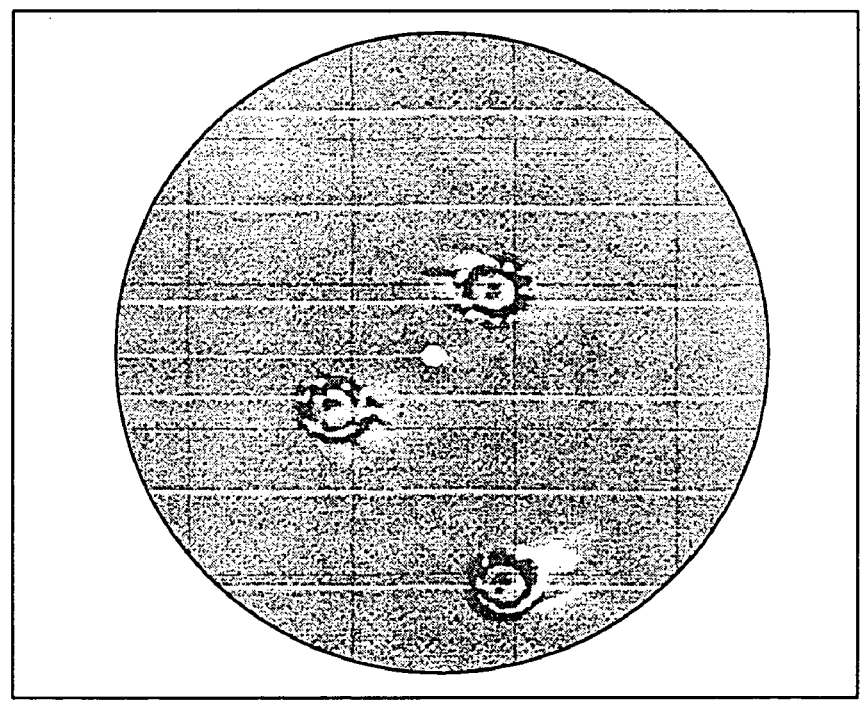

The imaging system 10 has been used for a variety of surface analysis experiments. FIGS. 10A, 10B, 11A and 11B show sample wafer images that were generated using the NVCPD sensor 12 imaging for wafer inspection. The images show optical images in FIG. 10A and 11A and NVCPD images in FIG. 10B and 11B of a 100 mm form of the wafers 15. The first wafer 15 was cleaned, and then a small vacuum pick-up device was attached to the surface of the wafer 15 in three locations. The optical image of FIG. 10A shows no evidence of any change on the surface 16 of the wafer 15. The NVCPD image of FIG. 10B shows a very large signal at the locations where the pick-up device was applied. The NVCPD signal is believed to be the result of a small amount of residue left on the surface 16 by the pick-up device.

Figure 11A:
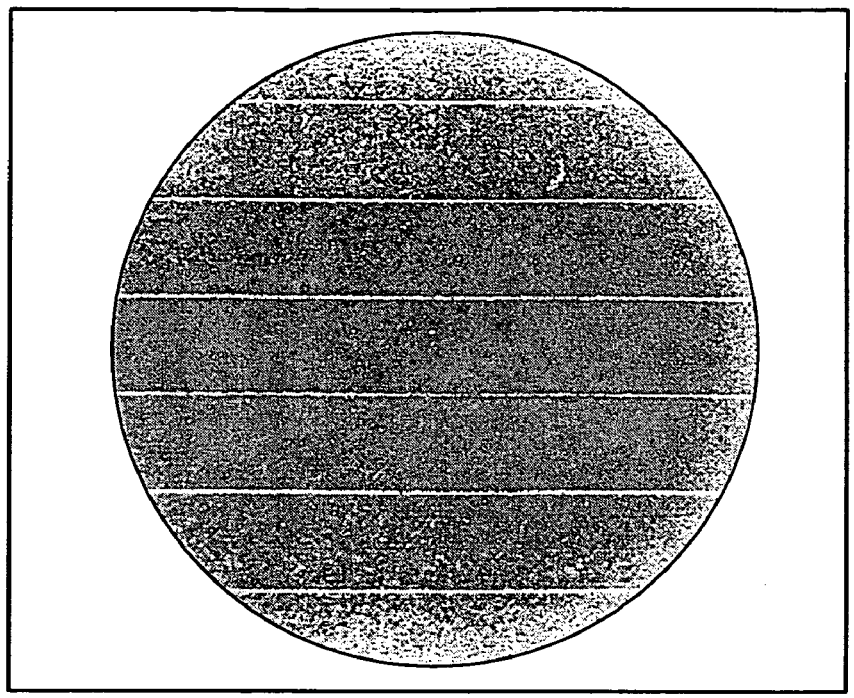
FIG. 11A illustrates an optical image of a second silicon wafer after applying alcohol while spinning the wafer and allowing the alcohol to dry and FIG. 11B is an NVCPD image of the same wafer of FIG. 11A.
Figure 11B:
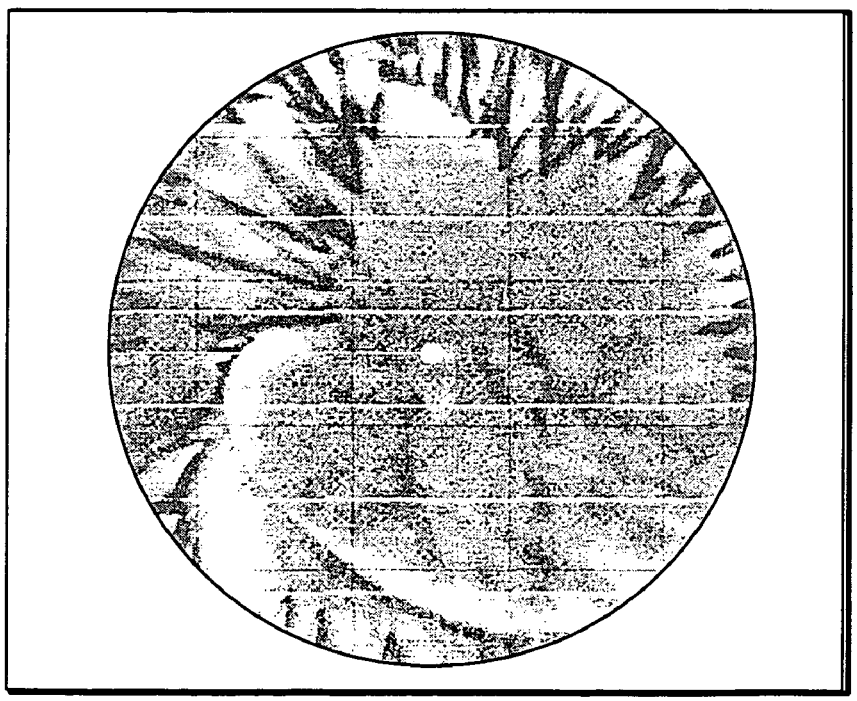

The second set of images in FIGS. 11A and 11B show a wafer 15 that has had alcohol spun-on and then dried. The resulting residue is not visible in the optical image FIG. 11A, but is clearly visible in the NVCPD image FIG. 11B. These images provide a clear demonstration of the usefulness of NVCPD sensor 12 for wafer inspection.

Figure 12A:
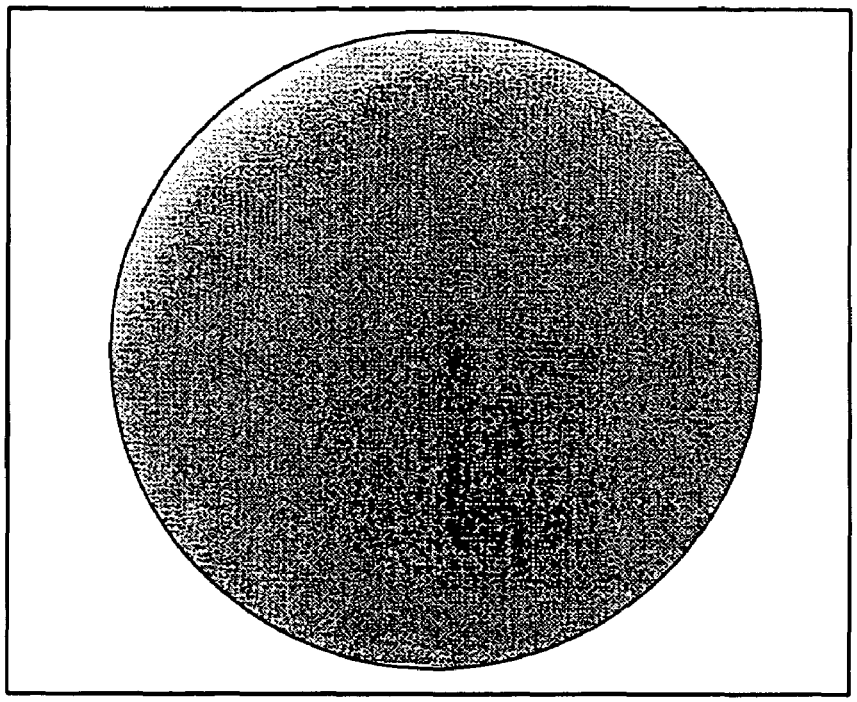
FIG. 12A illustrates an optical image of a silicon wafer after application of a latex glove mark and FIG. 12B is an NVCPD image of the same wafer of FIG. 12A.
Figure 12B:
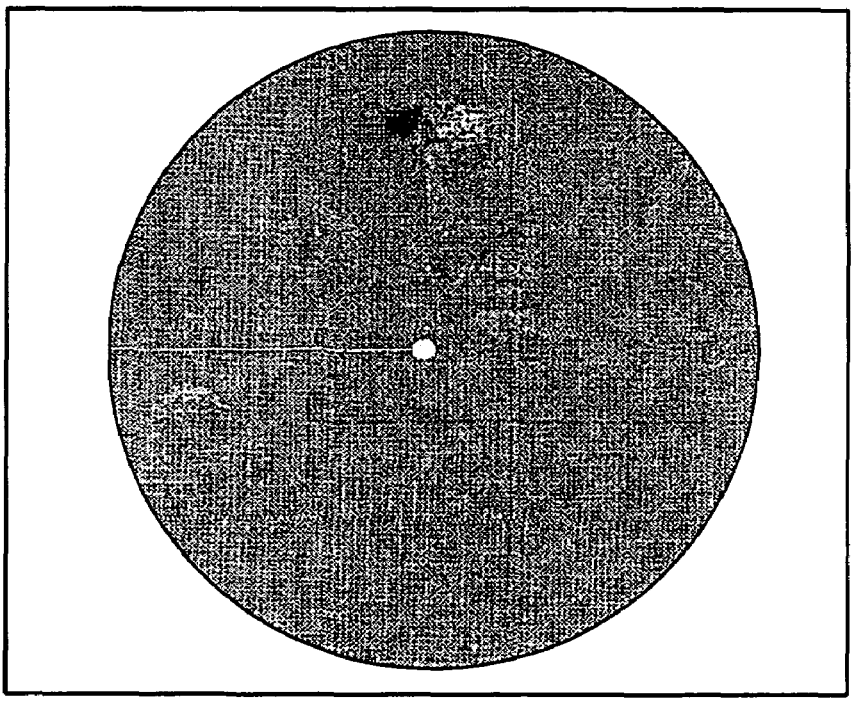
Figure 13A:
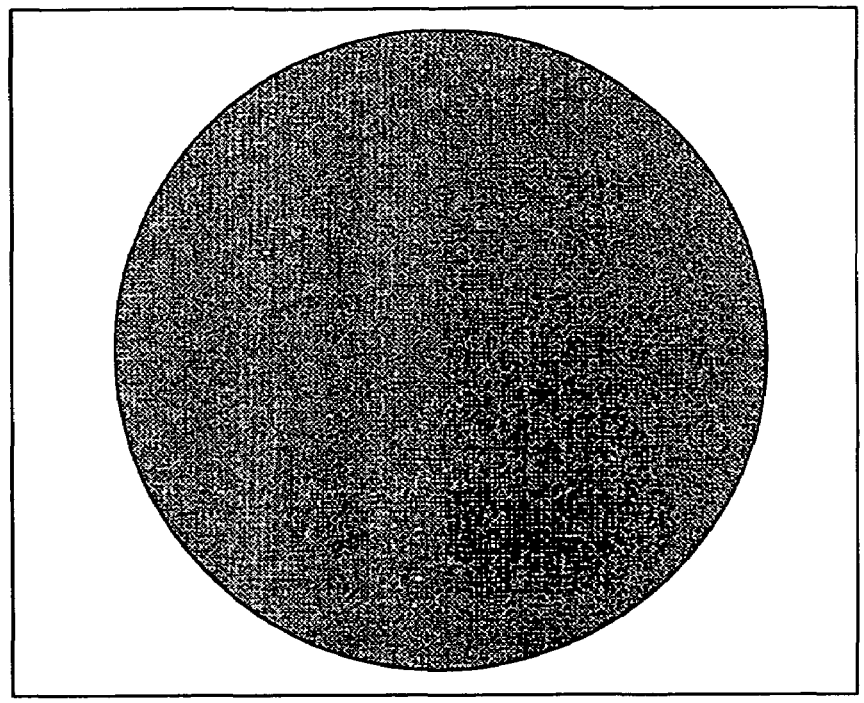
FIG. 13A illustrates an optical image of a silicon wafer having human fingerprints on the wafer and FIG. 13B illustrates an NVCPD image of the wafer of FIG. 13A.
Figure 13B:
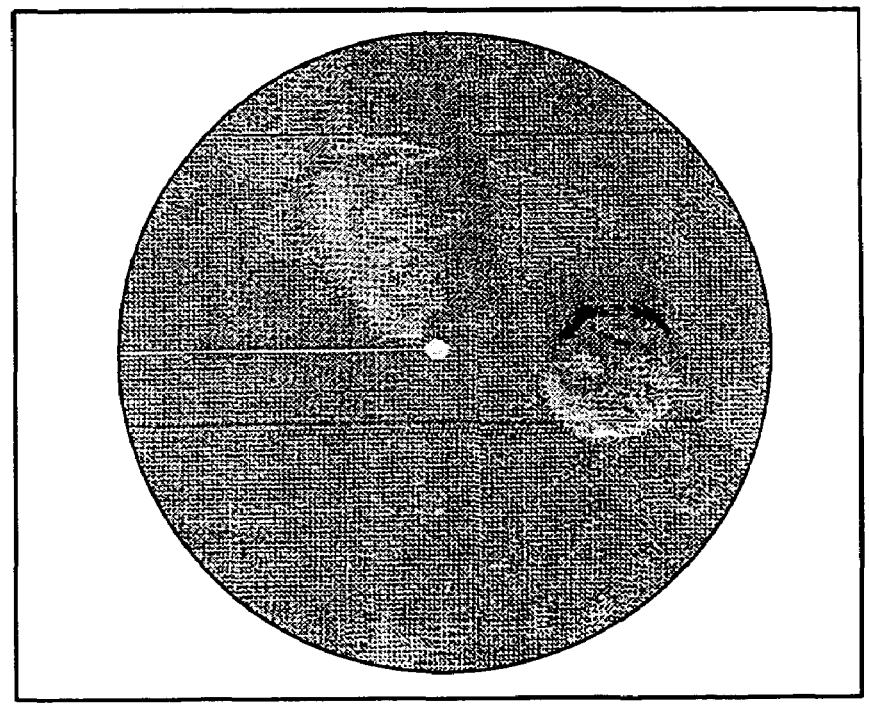
Figure 14:
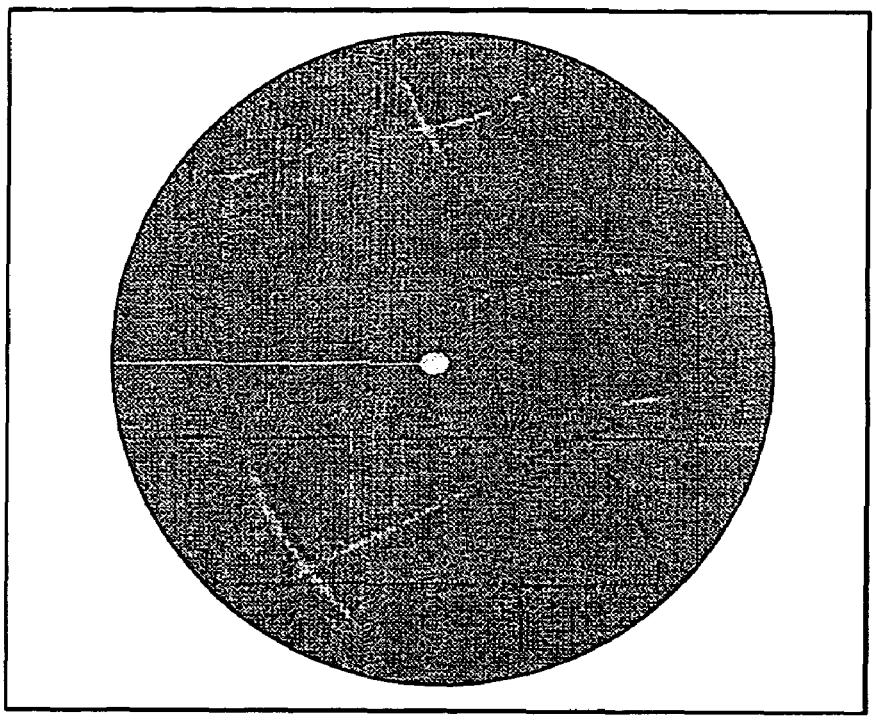
FIG. 14 illustrates an NVCPD image of a silicon wafer after brushing the wafer surface with a stainless steel tool.
Figure 15:
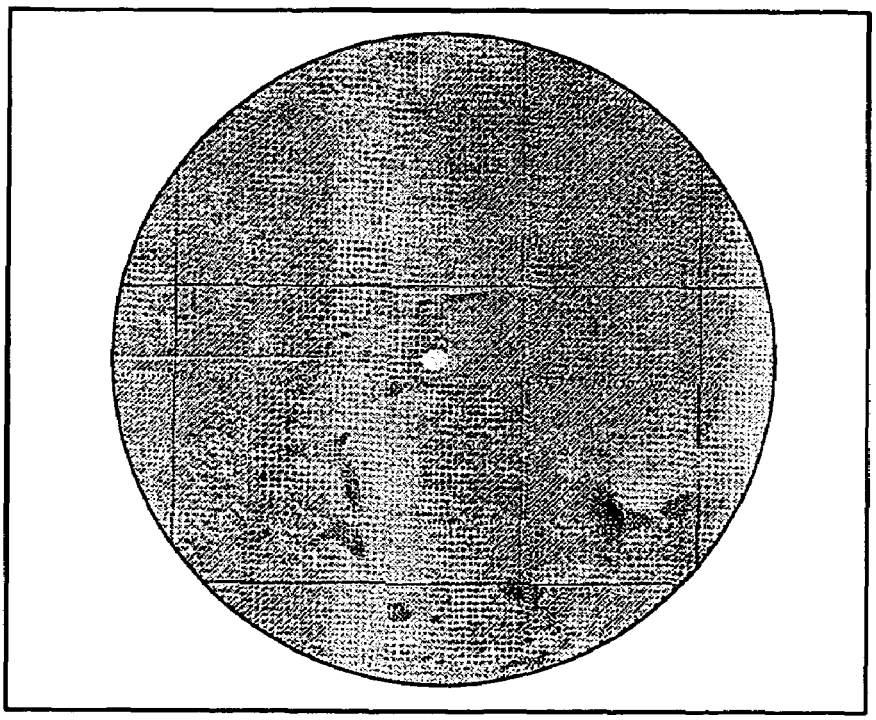
FIG. 15 illustrates an NVCPD image of a silicon wafer after pressing an aluminum fixture onto the wafer surface.

FIGS. 12A and 12B show, respectively, an optical image of latex glove marks and a NVCPD image of latex glove marks. FIGS. 13A and 13B show, respectively, an optical image of human fingerprints and an NVCPD image of the fingerprints. FIG. 14 shows a NVCPD image of a wafer 15 after brushing the wafer 15 with a stainless steel tool, and FIG. 15 shows a NVCPD image of the wafer 15 after pressing an aluminum fixture onto the wafer surface 16. All these example images were acquired using the NVCPD sensor 12 with the probe sensor tip 14 having a diameter of approximately 60 microns measured over a period of approximately 30 seconds.

While preferred embodiments of the invention have been shown and described, it will be clear to those skilled in the art that various changes and modifications can be made without departing from the invention in its broader aspects as set forth in the claims provided hereinafter.

What is claimed is:

1. An in-line analysis method for identifying a chemical defect present on a surface of a semiconductor wafer being processed in a clean room for production, comprising the steps of:

providing an in-line semiconductor wafer processing system including a semiconductor wafer scanning system for analyzing chemical defects;

providing a semiconductor wafer having a surface;

fixing the semiconductor wafer upon a wafer stage of the semiconductor wafer scanning system;

providing a non-vibrating contact potential difference sensor;

engaging a positioning mechanism in communication with the non-vibrating contact potential sensor whereby the non-vibrating contact potential difference sensor is positionable in relation to the wafer stage via the positioning mechanism and the non-vibrating contact potential difference sensor is positioned in the in-line semiconductor wafer processing system;

continuously radially scanning the non-vibrating contact potential difference sensor about a circumferential track of the semiconductor wafer;

generating contact potential difference track data from the non-vibrating contact potential difference sensor during at least the radial scanning of the semiconductor wafer relative to the sensor, the track data being representative of changes along the circumferential track of contact potential difference of the semiconductor wafer surface relative to the non-vibrating contact potential difference sensor;

outputting the track data for the track to a computer system for determining whether the track was a last track;

assembling the contact potential difference track data for each scanned track to form representative contact potential difference track data representative of the semiconductor wafer surface;

processing the non-vibrating contact potential difference track data to automatically detect a pattern that represents a chemical defect or chemical non uniformity present on the semiconductor wafer surface;

processing the pattern to automatically identify the category of defect or non uniformity detected; and outputting a large area spatial image, having a resolution of at least about 60 microns, of the semiconductor wafer surface, illustrating spatial location of the chemical defect or chemical non uniformity on the semiconductor wafer surface.

2. The method as defined in claim 1 where the semiconductor wafer includes at least one additional layer disposed on a base silicon wafer.

3. A method for identifying a defect present on a surface of a semiconductor wafer being processed for production, comprising the steps of:

providing a semiconductor wafer processing system including a semiconductor wafer scanning system for analyzing defects;

providing a semiconductor wafer having a surface;

fixing the semiconductor wafer upon a wafer stage of the semiconductor wafer scanning system;

providing a contact potential difference sensor;

engaging a positioning mechanism in communication with the contact potential sensor whereby the contact potential difference sensor is positionable in relation to the wafer stage via the positioning mechanism and the contact potential difference sensor is positioned in the in-line semiconductor wafer processing system;

continuously radially scanning the contact potential difference sensor about a circumferential track of the semiconductor wafer;

generating contact potential difference track data from the contact potential difference sensor during at least the radial scanning of the semiconductor wafer relative to the sensor with the track data being representative of changes along the circumferential track of contact potential difference of the semiconductor wafer surface relative to the contact potential difference sensor;

processing the contact potential difference track data for selected ones of the scanned track to form representative contact potential difference track data representative of the semiconductor wafer surface; and processing the contact potential difference track data to automatically detect a pattern that represents a defect.

4. The method as defined in claim 2, further including the steps of:

displaying the contact potential difference track data on a display to generate a characteristic wafer image; and comparing the characteristic wafer image with standard images of defects to identify a category of the defect present on the surface of the semiconductor wafer.

5. The method as defined in claim 3 wherein the standard images of defects are selected from the group of a scratch, a metal contaminated wafer image, an alcohol contaminated wafer image, a vacuum pick up damaged wafer image, a latex contaminated wafer image, a chemical contamination and a human fingerprint contaminated wafer image.

6. The method as defined in claim 2, wherein the step of processing the sensor data includes processing the track data into an image that is displayed to the user for evaluation by the user.

7. The method as defined in claim 2 wherein the step of processing the track data includes automatically processing the track data to identify the category of defect detected.

8. The method as defined in claim 2 wherein the step of continuously radially scanning the semiconductor wafer comprises spinning the wafer.

9. A method of detecting at least one of chemical, physical and electrical non-uniformities on a wafer surface comprising the steps of:
providing a wafer having a surface;
providing a contact potential difference sensor having a probe tip;
scanning the wafer surface laterally relative to the contact potential difference sensor;
generating sensor data representative of changes in the contact potential difference between the sensor probe tip and the wafer surface as the sensor probe tip scans laterally across different locations on the wafer surface; and
processing the contact potential difference sensor data to detect a pattern that represents a defect.

10. The method as defined in claim 9 further comprising the use of the sensor data to generate a graphical display of the wafer surface including a visual indication of the location of the defect.

11. The method as defined in claim 9 further comprising the step of generating an image representative of the change in the contact potential difference at different locations on the wafer surface.

12. The method as defined in claim 9 where the change in contact potential difference is representative of a change in copper states on the wafer surface.

13. The method as defined in claim 9 where the wafer is selected from the group of silicon and glass.

14. The method as defined in claim 9 where the change in contact potential difference is representative of changes in the roughness of the wafer surface.

15. The method as defined in claim 9 where the non-vibrating contact potential difference sensor is used to detect a mechanical structure on the edge of the wafer.

16. A method of detecting a chemical contaminant on a semiconductor wafer surface during processing of a semiconductor wafer, comprising the steps of:
providing a semiconductor wafer having a surface;
providing a semiconductor wafer processing system including a semiconductor wafer scanning system;
positioning the semiconductor wafer in the semiconductor wafer scanning system;
positioning a contact potential difference sensor in operational relationship with the semiconductor wafer;
moving the contact potential difference sensor and the semiconductor wafer relative to each other in a lateral scanning manner;
generating from the lateral movement of the semiconductor wafer relative to the contact potential difference probe a signal output representative of the changes in contact potential between the contact potential difference sensor and the semiconductor wafer as the relative lateral motion occurs, thereby providing scanning data representative of the changes in the contact potential difference across the semiconductor wafer relative to the contact potential difference sensor;
processing the scanning data to locate areas of high contact potential difference variability characteristic of changes in a chemical state of the semiconductor wafer; and
comparing the scanning data to known contact potential difference data sets to determine whether the semiconductor wafer contains any chemical contaminant.

17. The method as defined in claim 16 wherein the step of processing comprises performing a pattern recognition methodology to determine a category of the chemical contaminant.

18. The method as defined in claim 17 further including the step of processing the wafer with a treatment for ameliorating the category of the chemical contaminants identified.

19. The method as defined in claim 16 further including the step of performing a supplementary analysis of the scanning data.

20. The method as defined in claim 19 wherein the step of performing a supplementary analysis of the scanning data includes analyzing the chemical contaminants.

21. The method as defined in claim 16 further including the step of applying a computerized decisional methodology to reject selected ones of the semiconductor wafers having selected ones of the chemical contaminant.

22. A system for in-line semiconductor wafer processing comprising:
a semiconductor wafer processing system to identify a defect on a semiconductor wafer, the processing system including a wafer scanning system;
a semiconductor wafer;
a semiconductor wafer stage of the wafer scanning system for receiving the semiconductor wafer, the semiconductor wafer stage being rotatable and engageable with the semiconductor wafer;
a contact potential difference semiconductor sensor system having a contact potential difference probe;
a positioning assembly in communication with the contact potential difference probe whereby the contact potential difference probe can be positioned relative to the semiconductor wafer secured on the semiconductor wafer stage;
a scanning assembly to laterally scan the semiconductor wafer relative to the contact potential difference probe;
the contact potential difference probe adapted to produce a signal characteristic of the defect on the semiconductor wafer in response to a change in the contact potential difference generated by relative lateral scanning motion of the contact potential difference probe and the semiconductor wafer;
a computer in communication with the contact potential difference probe of the scanning system, whereby relative contact potential difference data is output by the contact potential difference probe to the computer; and
a visual image characteristic of the defect and its spatial distribution on the semiconductor wafer generated by the computer and representative of the contact potential difference data.

23. The system as defined in claim 22 further including a data base of contact potential difference data for standard defects, the computer including computer software which can analyze the relative contact potential difference data and compare with the standard defect contact potential data to generate identification information about the type of defect and the spatial distribution present on the surface of the semiconductor wafer.

24. The system as defined in claim 22 further including a transport device to move the semiconductor wafer to a secondary processing system for remediation.

25. The system as defined in claim 22 further including a plurality of contact potential difference probes with one of the probes disposed immediately downstream from each of a plurality of cleaning systems, thereby enabling monitoring of the semiconductor wafer after processed at each of the cleaning systems.

26. The system as defined in claim 25 further including a downstream processing system for determining time necessary to clean the semiconductor wafer.

27. The system as defined in claim 22 that includes a system for automatically determining type of chemical contaminants on the semiconductor wafer and modifying cleaning parameters to improve a state of chemical cleanliness for the semiconductor wafer.

28. The system as defined in claim 22 further including computer software executed by the computer analyzing the contact potential difference data to determine defects selected from the group of mechanical defects, chemical contaminants, thin dielectric films and electrical non-uniformities.

* * * * *